United States Patent [19]

Brown et al.

[11] Patent Number: 6,060,050
[45] Date of Patent: May 9, 2000

[54] PROBIOTIC COMPOSITIONS

[75] Inventors: Ian L Brown, Tamworth; Kenneth J McNaught, Cottage Point; Robert N Ganly, Kew; Patricia Lynne Conway, La Perouse; Anthony John Evans, Pennant Hills; David Lloyd Topping, Glenelg North; Xin Wang, Randwick, all of Australia

[73] Assignees: The University of New South Wales, Kensington; Burns Philp & Company Limited; Burns Philp Research & Development PTY Limited, both of Sydney; Gist-Brocades Australia PTY Limited, Moorebank; Commonwealth Scientific and Industrial Research Organisation, Victoria; Arnott's Biscuits Limited, Homebush; Goodman Fielder Ingredients Limited, Gladesville; Goodman Fielder Limited, Sydney, all of Australia

[21] Appl. No.: 08/793,892

[22] PCT Filed: Sep. 18, 1995

[86] PCT No.: PCT/AU95/00613

§ 371 Date: Jun. 17, 1997

§ 102(e) Date: Jun. 17, 1997

[87] PCT Pub. No.: WO96/08261

PCT Pub. Date: Mar. 21, 1996

[30] Foreign Application Priority Data

Sep. 16, 1994 [AU] Australia .................. PM8230

[51] Int. Cl.$^7$ ........................................ A01N 63/00
[52] U.S. Cl. ................ 424/93.3; 424/93.4; 424/93.45
[58] Field of Search .................. 424/93.3, 93.4, 424/93.45

[56] References Cited

FOREIGN PATENT DOCUMENTS

| 203586 | 12/1986 | European Pat. Off. . |
| 287699 | 10/1988 | European Pat. Off. . |
| 86/02837 | 11/1985 | WIPO . |

OTHER PUBLICATIONS

Cailxto et al., Grasas Aceites, 42(3): 239–242, 1991.

O'Keefe, Scandinavian Journal of Gastroenterology, Supplement, 220:52–59, 1996.

Tomlin et al. British Journal of Nutrition, 64:589–595, 1990.

*Primary Examiner*—Jean C. Witz
*Attorney, Agent, or Firm*—McDermott, Will & Emery

[57] ABSTRACT

A probiotic composition is disclosed which is particularly useful for inclusion in food products to enhance their nutritional value. The composition comprises one or more probiotic microorganisms such as Bifidobacterium and a carrier to transport the microorganisms to the large bowel or other regions of the gastrointestinal tract. The carrier is a modified or unmodified resistant starch, particularly a high amylose starch, which acts as a growth or maintenance medium for microorganisms in the large bowel or other regions of the gastrointestinal tact.

19 Claims, 7 Drawing Sheets

PROBIOTIC COMPOSITIONS

FIELD OF THE INVENTION

This invention relates to nutritional compositions, particularly compositions for the delivery and maintenance of probiotic microorganisms to and in the gastrointestinal tract, especially the large bowel. As used in this specification, probiotics or probiotic microorganisms is a live microbial feed supplement which beneficially affects the host animal by improving its intestinal microbial balance. This is the definition provided by R. Fuller (AFRC Institute of Food Research, Reading Laboratory, UK) in—Journal of Applied Bacteriology, 1989. 66, pp.365–378. "Probiotics in Man and Animals—A Review"

BACKGROUND TO THE INVENTION

It is the contention of many scientists that the health and wellbeing of people can be positively or negatively influenced by the microorganisms which inhabit the gastrointestinal tract, and in particular, the large bowel. These microorganisms through the production of toxins, metabolic by-products, short chain fatty acids, and the like affect the physiological condition of the host. The constitution and quantity of the gut microflora can be influenced by conditions or stress induced by disease, life style, travel, and other factors. If microorganisms which positively affect the health and wellbeing of the individual can be encouraged to populate the large bowel, this should improve the physiological wellbeing of the host.

The introduction of beneficial micro-organisms, or probiotics, is normally accomplished by the ingestion of the organisms in drinks, yoghurts, capsules, and other forms in such a way that the organism arrives in a viable condition in the large bowel.

It has been demonstrated by Englyst H. N. et al (1987) "Polysaccharides breakdown by mixed populations of human faecal bacterial", EMS Microbiology Ecol 95: 163–71, that the bacterial fermentation of resistant starch in the large bowel produces elevated levels of short chain fatty acids, particularly beneficial types such as propionate and butyrate.

The present inventor has realised that it would be desirable to not only deliver probiotic microorganisms to the large bowel but also to provide a medium that would function to promote the growth of the microorganisms when they reach the large bowel.

Surprisingly, it has been found that modified or unmodified resistant starches may function both as a means to transport the probiotic microorganisms to the large bowel and as a growth medium for the microorganism delivered to the target region of the large bowel. As used in this specification, "resistant starch" includes those forms defined as RS1, RS2, RS3 and RS4.

DISCLOSURE OF THE INVENTION

Accordingly, this invention consists in a probiotic composition comprising one or more probiotic microorganisms and a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for microorganisms in the large bowel or other regions of the gastrointestinal tract.

In another aspect the present invention further consists in a two part composition comprising a first part which includes one or more probiotic microorganisms and a second part which includes a carrier, the carrier comprising a modified or unmodified resistant starch or mixtures thereof, which carrier acts as a growth or maintenance medium for microorganisms in the large bowel or other regions of the gastrointestinal tract.

In one broad aspect, the resistant starch functions as a carrier to transport the probiotic microorganisms to the large bowel. The introduction of those microorganisms into the large bowel is beneficial as previously explained. In addition, the resistant starch when present in the large bowel will function as a nutritional source for microorganisms already present in the large bowel.

In a narrower aspect, some probiotic microorganisms may be selected such that they are able to utilise the resistant starch as a nutritional source. Thus the: resistant starch will function both as a carrier and a nutritional source for those probiotic microorganisms.

There are a variety of probiotic microorganisms which are suitable for use in this invention including yeasts such as Saccharomyces, and bacteria such as the genera Bifidobacterium, Bacteroides, Clostridium, Fusobacterium, Propionibacterium, Streptococcus, Enteroccus, Lactococcus, Staphylococcus, Peptostrentococcus and Lactobacillus. The invention is not, however, limited to these particular microorganisms. The person skilled in the art would understand and recognise those microorganisms which may be included in the compositions of the invention. Specific strains that have been tested and found suitable for use in this invention are set out in Table 1.

TABLE 1

| Bacterial Name | Strain Number |
| --- | --- |
| Bifidobacterium. adolescentis | 248 UNSW 509400 |
| Bif. bifidum | 248 UNSW 509800 |
| Bif. longum | 248 UNSW 509700 |
| Bif. pseudolongum | 248 UNSW 509500 |
| Bif. infantis | 248 UNSW 510000 |
| Bacteroides fragilis | NCTC 9343 |
| Bact. vulgatus | 1ATCC 8482 |
| Lactobacillus viridescens | 1ATCC 12706 |
| L. casei | 1ATCC 25302 |
| L. acidophilus | 1ATCC 4356 |
| L. plantarum | 1ATCC 8014 |
| L. casei subsp. rhamnosus | 1ATCC 7469 |
| L. fermentum | 1ATCC 9338 |
| L. brevis | 248 UNSW 055100 |
| L. salivarius | 1ATCC 11741 |

The probiotic microorganisms may be used in this invention in a variety of forms including concentrates, frozen concentrates and freeze-dried material.

In one preferred form, probiotic microorganisms may be freeze-dried as a suspension with the resistant starch. For compositions of this type, the resistant starch may act as a cryoprotectant.

Typically, the resistant starch may be incorporated at a level of 2–20% w/w. Depending on the amount of resistant starch added, the drying rate and final products' consistency and rehydration characteristics will be affected. A level of about 5% of total dry solids will be typically used, although higher concentrations may be used to improve dry cake properties.

In another form, probiotic microorganisms may be used as freeze-dried material with resistant starch in an extrusion process to form a granular product. To prepare this form of composition, it is important to ensure that the temperature of the extrusion is not so high as to adversely affect the viability of the microorganisms. One way to achieve this is to feed resistant starch together with a higher melting point fat into an extruder with zones kept at a temperature sufficiently high to maintain the material in molten form. In subsequent, cooler zones of the extruder, a suspension of probiotic microorganism together with a lower melting point fat is fed. This results in an effective mixing with the fat and resistant starch blend. Extrusion then occurs through a suitably chilled die. The molten fat may be an hydrogenated vegetable oil or a blend of hydrogenated and non-hydrogenated vegetable oils, such as palm oil, which has a melting point of more than 50° C. but with a high plasticity in the region of about 35° C. to 40° C. Desirably the oil(s) should be stable and non-oxidising.

The rate of blending of the low melting point fat or oil into the extruder may be in the range of 0 to 10%. Higher amounts may be used where particular characteristics such as improved distribution through the food matrix are required.

Other ingredients may be added to stabilise the blend.

The mixture of resistant starch to probiotic microorganism may be in any ratio, preferably at least 1:1:1 (resistant starch:bacteria in freeze dried form:oil/fat). By altering the ratio of resistant:oil/fat, the flowability of the blend may be improved.

In another form, probiotic microorganisms may be micro-encapsulated with resistant starch. A typical process of micro-encapsulation requires the preheating of a low melting point oil, typically at less than 50° C., preferably less than 40° C., above its melting point. Under conditions of low shear, an amount of freeze dried probiotic microorganisms, such as 10%, are added and dispersed. Resistant starch in an amount of for example 20% of oil is added together with other ingredients and binding agents such as gelatin and gums.

The dispersion is then sprayed into the head of a cooling tower to allow uniform particles with an average size typically in the range 20–200 microns (depending on application) to form and harden.

The viable cell counts of final micro-encapsulated product may be of the order $10^8$–$10^{12}$ microorganisms per gram. In addition to the forms monitored above, the probiotic microorganisms may be presented in other forms including blending, spray cooling, entrapment and adhesion.

In general terms, the probiotic microorganisms will be included with the resistant starch in a ratio of about $10^2$ cfu per g resistant starch or more, preferably about $10^5$ or more, most preferably about $10^7$ or more. As a maximum, generally nor more than about $10^{12}$ cfu per gram resistant starch will be used.

Either modified or unmodified resistant starches or mixtures thereof are used in this invention. The advantage of resistant starch in a probiotic composition is that it is not digested until it reaches the large bowel. Therefore it provides a readily available substrate for fermentation by the probiotic microorganisms as soon as they arrive in the large bowel. In both cases, a preferred form of resistant starch is a high amylose starch particularly high amylose starches as disclosed and taught in WO94/03049 and WO94/14342, the contents of which are incorporated into this specification for the purposes of convenient cross-reference.

In WO94/03049 and WO94/14342, high amylose starches are disclosed which are resistant starches and include maize starch having an amylose content of 50% w/w or more, particularly 80% w/w or more, rice starch having an amylose content of 27% ww or more and; particular granular size ranges of starches having an amylose content of 50% or more and enhanced resistant starch content, these starches including maize, barley, wheat and legumes. This invention is not, however, limited to these forms of resistant starch. For example, other forms of resistant starch are derived from sources such as bananas and potatoes.

The compositions of the invention may be prepared such that probiotic microorganisms and carrier are presented in combination. Alternatively, the probiotic microorganism and the carrier may be presented in each of two separate parts. In this form, either the part containing the probiotic microorganisms or the part containing the carrier may be consumed first, followed by the other part shortly thereafter.

In an unmodified form, the resistant starch will serve as a substrate for fermentation by the probiotic microorganisms when the composition reaches the large bowel.

It may be advantageous to also chemically modify the starch to, for instance, alter the charge density or hydrophobicity of the granule and/or granule surface to enhance the attachment compatibility between the microorganism and the resistant starch. Chemical modifications, such as etherification, esterification, acidification and the like are well known in this art as being suitable chemical treatments.

It may also be useful to modify the degree of enzyme susceptibility of the resistant starch by altering the conformation or structure of the starch. Examples include acid or enzyme thinning and cross bonding using difunctional reagents.

One useful modification is the amylolysis of high amylose starches to give starch granules characterised by pits or erosions which can extend from the surface to the interior of the granules. These pits allow the entry of enzymes to the more enzyme susceptible core of the starch granule which is solubilised.

Eroded starch granules not only have increased surface area for the attachment of microorganisms, they also allow for the encapsulation and entrapment of microorganisms within the interior of the granule. This latter property assists in the protection of microorganisms thereby facilitating transport to the large bowel.

It is also within the scope of this invention to subject enzymatically treated resistant starches to chemical modification as described above.

In addition to the aforementioned chemical, enzymatic and enzymatic/chemical modifications that may be made to the resistant starch, the probiotic microorganisms may be chemically attached to the resistant starch using materials such as difunctional reagents or polyfunctional reagents. Examples of reagents of these types are respectively gluteraldehyde and sodium trimetaphosphate.

This latter reagent is preferred as it is a food grade chemical.

Although the compositions of the invention may be directly ingested or used as an additive in conjunction with foods, it will be appreciated that they may be incorporated into a variety of foods and beverages including but not limited to yoghurts, ice creams, cheeses, baked products such as bread, biscuits and cakes, dairy and dairy substitute foods, confectionery products, edible oil compositions, spreads, breakfast cereals, juices and the like. Within the scope of the term "foods" are to be included in particular food likely to be classified as functional foods, i.e. "foods that are similar in appearance to conventional foods and are intended to be consumed as part of a normal diet, but have been modified to physiological roles beyond the provision of simple nutrient requirements" (NFA Policy Discussion Paper 7/94).

Similarly, the compositions of the invention may be presented in dosage forms such as in a capsule.

In general terms, the resistant starch in combination with the probiotic microorganisms will be presented in dry form. Suitable, but not limiting drying means include: spray drying, freeze drying and spouted bed drying.

MODES FOR CARRYING OUT THE INVENTION

One form that the resistant starch of this invention may take is when it is eroded or pitted. An example of the preparation of such starch will now be described with reference to FIGS. 4 to 7.

Preparation of Amylolysis Products from high Amylose Maize Starch Granules

A slurry containing 2000 grams of high amylose maize (Hi-maize-trade mark—obtained from Starch Australasia Ltd) starch (12.5% moisture) and water (7000 mL) was adjusted to pH 6.0 using sodium hydroxide solution (0.65M). The slurry was heated to 85° C. in a water bath. At this point in Experiments 2, 5 and 6 the thermo stable bacterial alpha amylase Termamyl was added. The experimental details are provided in Table 2.

After 60 minutes the temperature of the slurry was reduced to 60° C. and either (i) the pH adjusted to 4.5 using hydrochloric acid (10M), prior to the addition of the fungal glucoamylase and bacterial pullulanase blend Dextrozyme, or (ii) the pH was adjusted to 5.0 before the inclusion of the bacterial pullulanase Promozyme (Table 2). The slurry in both cases was maintained at 60° C. for 20 hours.

The pH was then raised to pH 6.0 using sodium hydroxide solution (0.65M) and the insoluble portion recovered using a Buchner funnel fitted with a Whatman 54 filter paper. The recovered material was washed with 7 litres of distilled water and then dried in a fan forced oven at 50° C.

| N.B. Termamyl - | thermo stable endo alpha amylase from *Bacillus licheniformis* |
| --- | --- |
| Pullalanase - | thermo stable pullulanase from Bacillus sp. |
| Glucoamylase - | from *Aspergillus niger* (all enzymes ex Novo Nordisk Bioindustrial Pty Limited) |

TABLE 2

CONDITIONS USED IN THE PREPARATION OF HIGH AMYLOSE MAIZE STARCH AMYLOLYSIS PRODUCTS

|  | Exp.2 | Exp.3 | Exp.4 | Exp.5 | Exp.6 |
| --- | --- | --- | --- | --- | --- |
| Starch Used (g) dsb | 1750 | 1750 | 1750 | 1750 | 1750 |
| Water (mls) | 7000 | 7000 | 7000 | 7000 | 7000 |
| Stage One |  |  |  |  |  |
| Temperature (° C.) | 85 | 85 | 85 | 85 | 65 |
| pH | 6.0 | 6.0 | 6.0 | 6.0 | 6.0 |
| Reaction Time (mins) | 60 | 60 | 60 | 60 | 6.0 |
| Novo Termamyl 120L (mL) | 4.00 | — | — | 2.00 | 2.00 |
| Stage Two |  |  |  |  |  |
| Temperature (° C.) | 60 | 60 | 60 | 60 | 60 |
| pH | 5.0 | 5.0 | 5.0 | 5.0 | 5.0 |
| Reaction Time (hrs) | 20 | 20 | 20 | 20 | 20 |
| Novo Dextrozyme (mL) | — | — | — | 2.00 | — |
| Novo Promozyme 200L (mL) | — | 10.00 | 2.50 | — | 2.50 |
| Amount recovered (g) | 735 | 1555 | 1549 | 1020 | 1012 |

*Exp. = Experiment

Dietary fibre and resistant starch levels were determined for the starches of each of these experiments, the results of which are shown in Table 3.

TABLE 3

TOTAL DIETARY FIBRE AND RESISTANT STARCH LEVELS IN HIGH AMYLOSE MAIZE STARCH AMYLOLYSIS PRODUCTS

|  | Total Dietary Fibre (%) dsb | Resistant Starch McCleary et al (%) dsb |
| --- | --- | --- |
| High Amylose Maize Starch | 33.4 | 18.1 |
| High Amylose Maize Starch Residues After Amylolysis |  |  |
| Experiment 2 | 37.0 | 36.0 ± 2.9 |
| Experiment 3 | 31.4 | 30.1 ± 2.0 |
| Experiment 4 | 34.4 | 29.3 |
| Experiment 5 | 35.8 | 34.7 |
| Experiment 6 | 39.3 | 42.0 ± 0.9 |

* dsb = dry solids basis

In each case, it is evident that the enzyme treatment has resulted in a substantial enhancement of the resistant starch content while dietary fibre levels have been essentially maintained.

Figure 1:
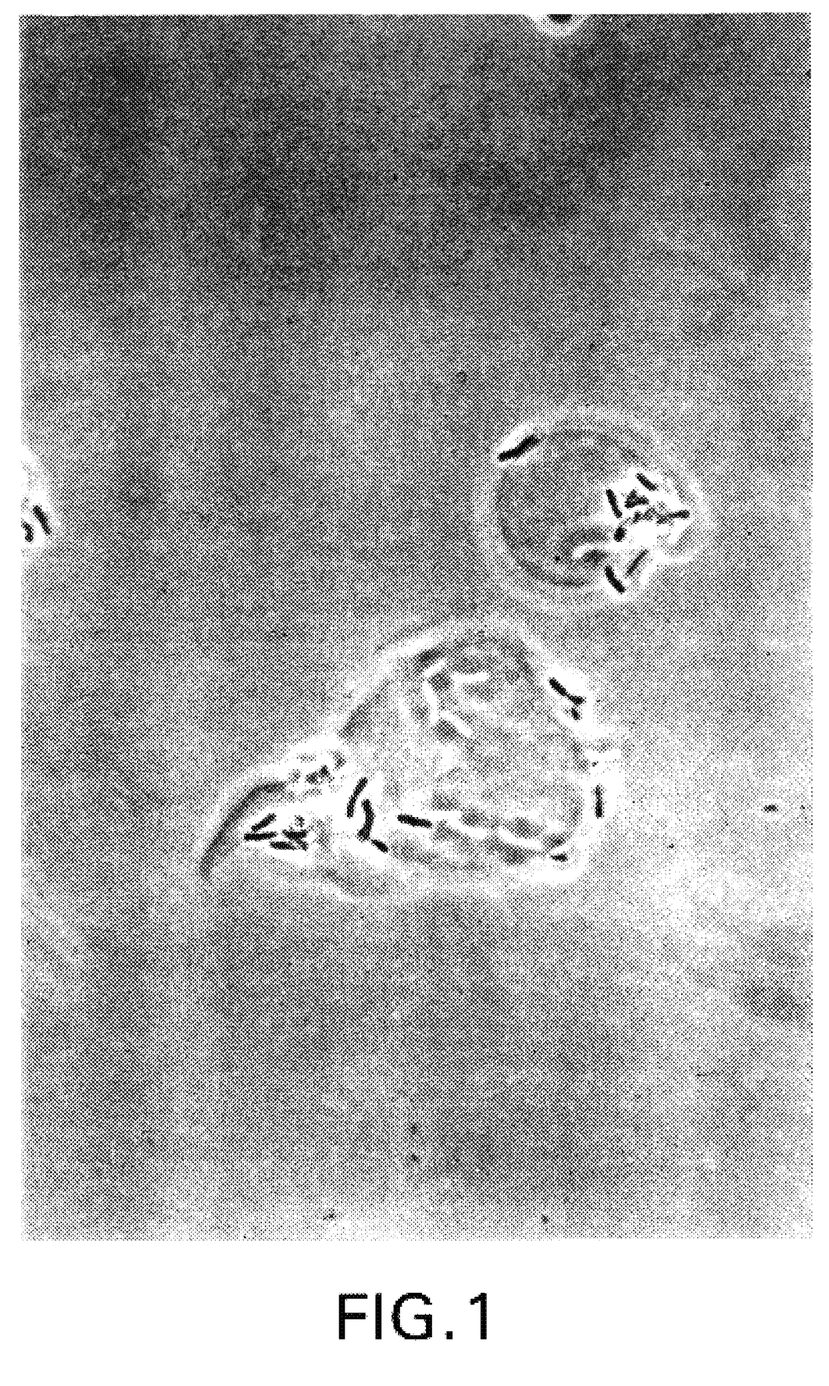
FIG. 1 is a light microscopic photograph of Bifidobacterium associated with a source of resistant starch (high amylose starch granules) prior to anaerobic incubation at 37° C.
Figure 2:
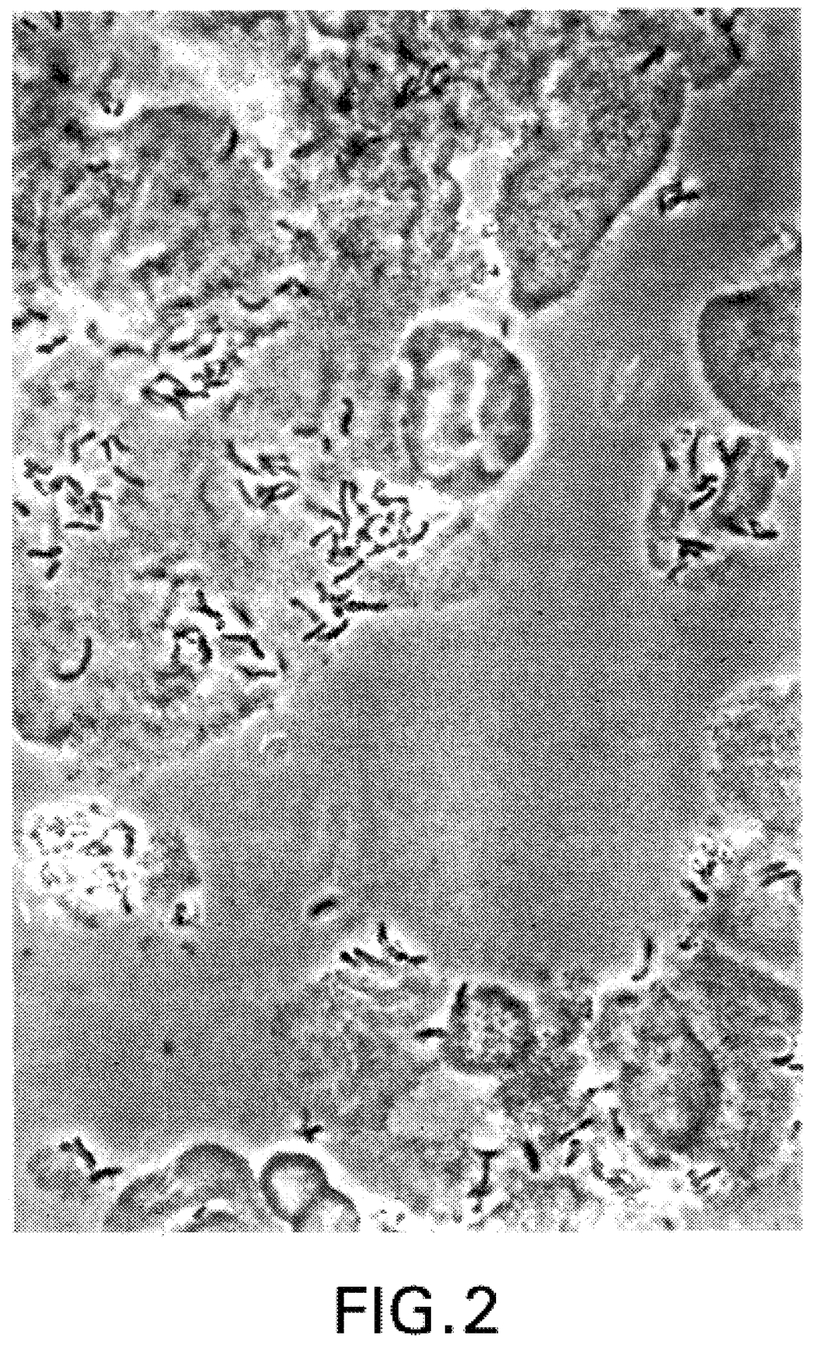
FIG. 2 is a light microscopic photograph as in FIG. 1 after incubation.
Figure 3:
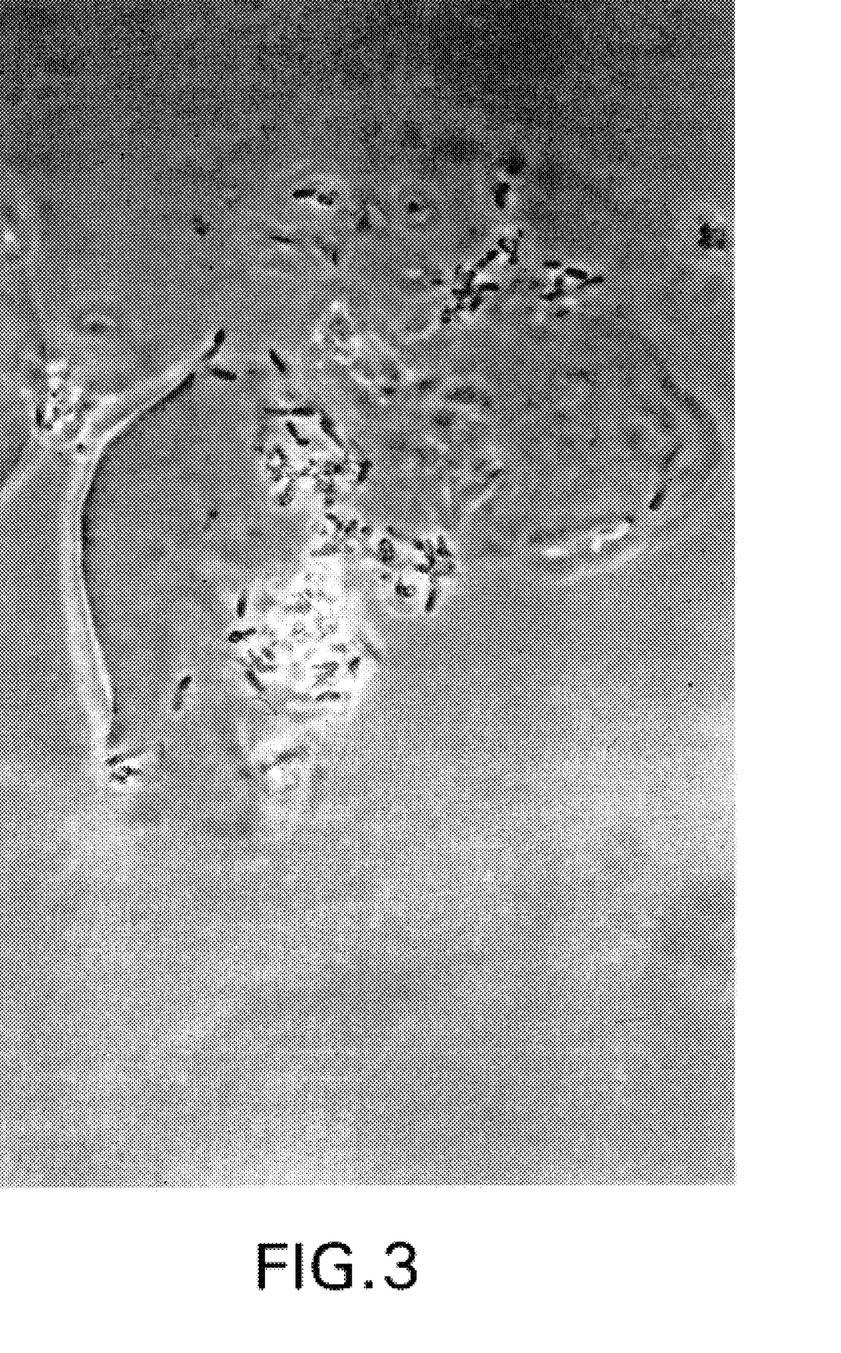
FIG. 3 is a light microscopic photograph as in FIG. 1 after degradation during incubation.
Figure 4:
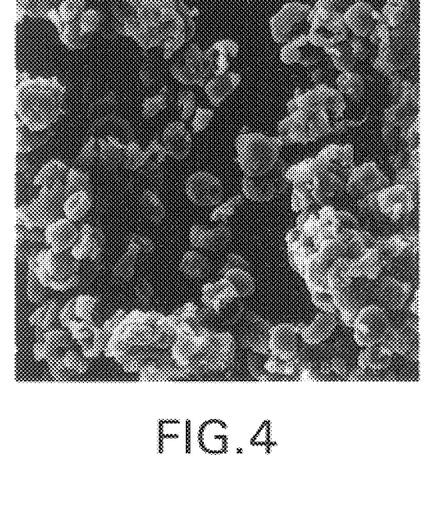
FIG. 4 is a scanning electron photomicrograph showing intact resistant starch (high amylose starch granules)
Figure 5:
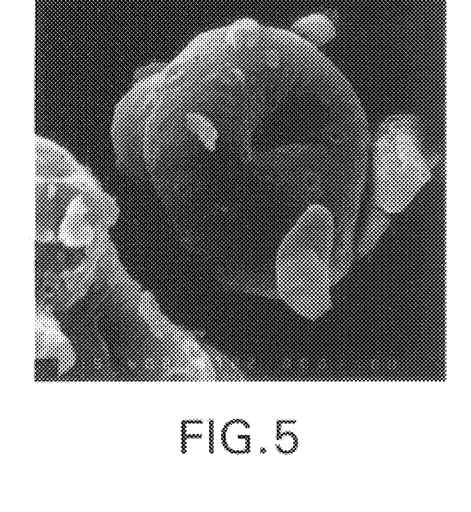
FIG. 5 is a scanning electron photomicrograph showing external erosion of the starch granule as a result of treatment with thermostable bacterial alpha amylase and pullulanase.
Figure 6:
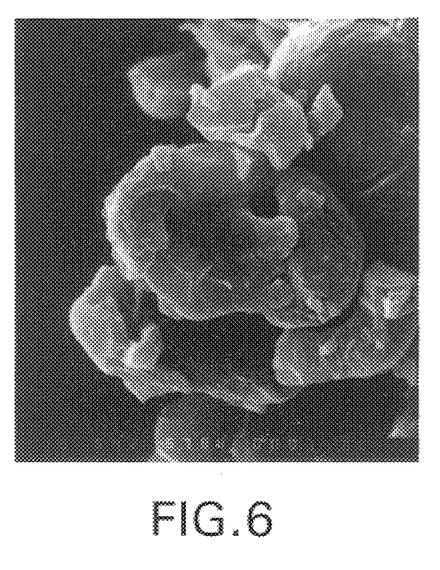
FIG. 6 is a scanning electron photomicrograph of an enzyme treated starch granule fracturing about the pit.
Figure 7:
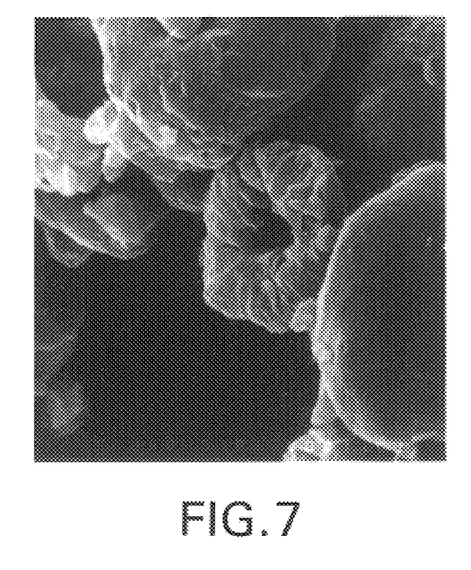
FIG. 7 is a scanning electron photomicrograph of a fractured enzyme treated granule displaying a hollow core region.

The results of such enzyme treatments are clearly shown in the accompanying FIGS. 5, 6 and 7, particularly when compared with the untreated starch granules of FIG. 4.

Modified starches prepared in this way may be readily combined with probiotic microorganisms to form compositions of the invention.

An example of the preparation of an extruded form of the compositions of the invention will now be described.

Equipment Profile

Extruder screw profile of 5FS, 3FP (30°), 2RP (30°), 2FS, 5FP (60°), 3RP (60°), 3FS, 3FP (30°), 2RP (30°), 2FS, 3FP (30°), 2RP (30°), 3SLS

| Temperature Profile | |
|---|---|
| Zone 1 | (70°), |
| Zone 2 | (70°), |
| Zone 3 | (70°), |
| Zone 4 | (50°), |
| Zone 5 | (50°), |
| Zone 6 | (35°), |
| Zone 7 | (35°), |
| Zone 8 | (35°), |
| Die | 20 |

Method

Resistant starch is fed into an APV MPF 50.20 extruder at a feed rate of say, 20 kg/hr in conjunction with a molten fat, melting point of >50° C. The fat is kept liquid by recirculated hot water and delivered into the extruder in the second injection port at a rate of 2 kg/hr. A suspension of lyophilized bacteria, especially Bifidobacterium bifidum or Bif.Longum is prepared using a low melting point fat, eg, hydrogenated maize oil with a M.P. of 35–37° C., such that the fat is heated just above its melting point but not in excess and the lyophilized bacteria added and mixed thoroughly. This suspension is then fed into zone 7 of the extruder where it is mixed with the fat/starch blend, and then forced through a chilled die fitted with 2 mm diameter orifices. The material is granulated and further chilled to maintain its shape until used.

An example of a freeze dried form of the compositions of the invention will now be described.

Cell cultures, especially those of Bifidobacterium longum, Bifidobacterium bifidum or Cl.butyricum are produced by conventional means and a concentrated cell suspension prepared by membrane filtrating, preferably ultrafiltration and/or centrifugation. Resistant starch is gently stirred into the cell suspension (0.10–0.50 gm/ml) along with another cryoprotectant, sucrose (0.07 gm/ml). The product is then quickly frozen to −40° C. and freeze dried to a water activity of $a_w$ 0.01 or less to obtain optimum stability. The culture is then removed from the dryer, gently pulverised and packed into airtight containers and stored at 4° C. until use. Some examples of food products incorporating compositions of the invention are as follows:

| CITRUS-FLAVOURED BEVERAGE DRY MIX | |
|---|---|
| INGREDIENTS | % by Weight |
| Resistant starch | 9.00 |
| Freeze dried probiotic | 1.00 |
| Sucrose | 68.00 |
| Fieldose 17 Maltodextrin | 13.83 |
| Dextrose | 1.72 |
| Citric acid anhydrous | 1.00 |
| Flavour | 0.20 |
| Acacia gum | 0.25 |
| Tricalcium phosphate | 0.10 |
| Colour | To suit |
|  | 100.00 |

METHOD

1. Blend all ingredients thoroughly.

Preparation

With stirring, add 30 grams dry mix to 337 mls water.

Ingredients Supplier

Resistant starch (Hi maize) and Fieldose 17 are supplied by Starch Australasia Limited, Australia.

YOGHURT

The following formula is offered as a starting for the manufacture of stirred or set yoghurts.

| INGREDIENTS | % |
|---|---|
| Resistant starch | 10.0 |
| Whole Milk | 33.0 |
| Sugar | 10.5 |
| Non-fat Milk Solids | 9.0 |
| MAPS 449 | 0.5 |
| Stabilizer | 0.5 |
| Culture (probiotic) | 1.0 |
| Water | to 100.0 |

METHOD

1. Combine all of the ingredients except the culture, making sure that the stabilizer is well dispersed.
2. Heat the mixture to 88–93 degrees C., and hold at this temperature for 30 minutes.
3. Cool to 38–45 degrees C.
4. Add the resistant starch fraction.
5. Inoculate with the culture and incubate at 42 degrees C.
6. Allow the culture to ferment the yoghurt to a pH of 4.0–4.2.
7. Refrigerate at 5 degrees C.

NOTES:

1. There are a variety of stabilizers available consisting of gelatine, gelatine and gum blends or gum blends. Recommended stabilizers are a) Gelatine available from Leiner Davis Gelatin (Australia) Co., b) Sta-Rite and Stabilizer Gemcol ADQ available from Germantown Australia Co.
2. The stabilizer and MAPS 449 combination should be 1% w/w of the final mix. Higher concentrations can, under some circumstances, give adverse effects.
3. For stirred yoghurts, pumping and filling of the containers is done between Steps 6 and 7.
4. For set yoghurts, filling into the containers is done between Steps 5 and 6.
5. The Whole Milk can be substituted with Full Cream Milk Powder used at a level to give equivalent solids to those contributed by the Whole Milk. The quantity of water required is also adjusted accordingly.
6. For fruit flavoured yoghurts, commercial fruit bases are combined with the yoghurt prior to filling. A typical ratio would be 85 parts yoghurt to 15 parts fruit base.
7. If homogenization is required for textural purposes, it is recommended to lightly homogenize at 200–250 psi after Step 2, before cooling. Homogenization at lower temperatures could result in damage to the stabilizer component.

Ingredient supplier

Resistant starch (Hi maize) and MAPS 449 are supplied by Starch Australasia Limited, Australia.

| INSTANT MOUSSE | |
|---|---|
| INGREDIENTS | PARTS BY WEIGHT |
| Resistant Starch Fraction, Probiotic, Corn Syrup Solids | 15 parts |
| Fieldose 30 | 75 parts |
| Sugar | 50 parts |
| Instant Gelatin 800 | 4 parts |
| Instant FTD 176 Pregelatinized Starch | 10 parts |
| Water | 150 parts |
| Colour and Flavour | As required |

METHOD

Blend all of the dry ingredients.

Whilst stirring, add the dry mix to cold water.

Continue to whip until the over-run is 150%.

Ingredient Suppliers

Instant FTD 176, Fieldose 30 and resistant starch (Hi maize) are supplied by Starch Australasia Limited, Australia.

Instant Gelatin 800 is supplied by Leiner Davis Gelatin (Australia) Co.

In order to further assist in the understanding of this invention, a series of experiments will now be . described which demonstrate utility.

Experiment 1

In this experiment the ability of a range of colonic bacteria, obtained from culture collections and isolates from human faeces, to utilise a source resistant starch as a fermentation substrate was assessed. In all cases the source resistant starch was high amylose maize (Hi-maize-TM obtained from Starch Australasia Ltd) or derivatives thereof.

In Table 4, there is shown the fermentability results obtained for a range of resistant starch types and bacteria. Assessment was in terms of total carbohydrate residue (mg/mL).

Figure 8:
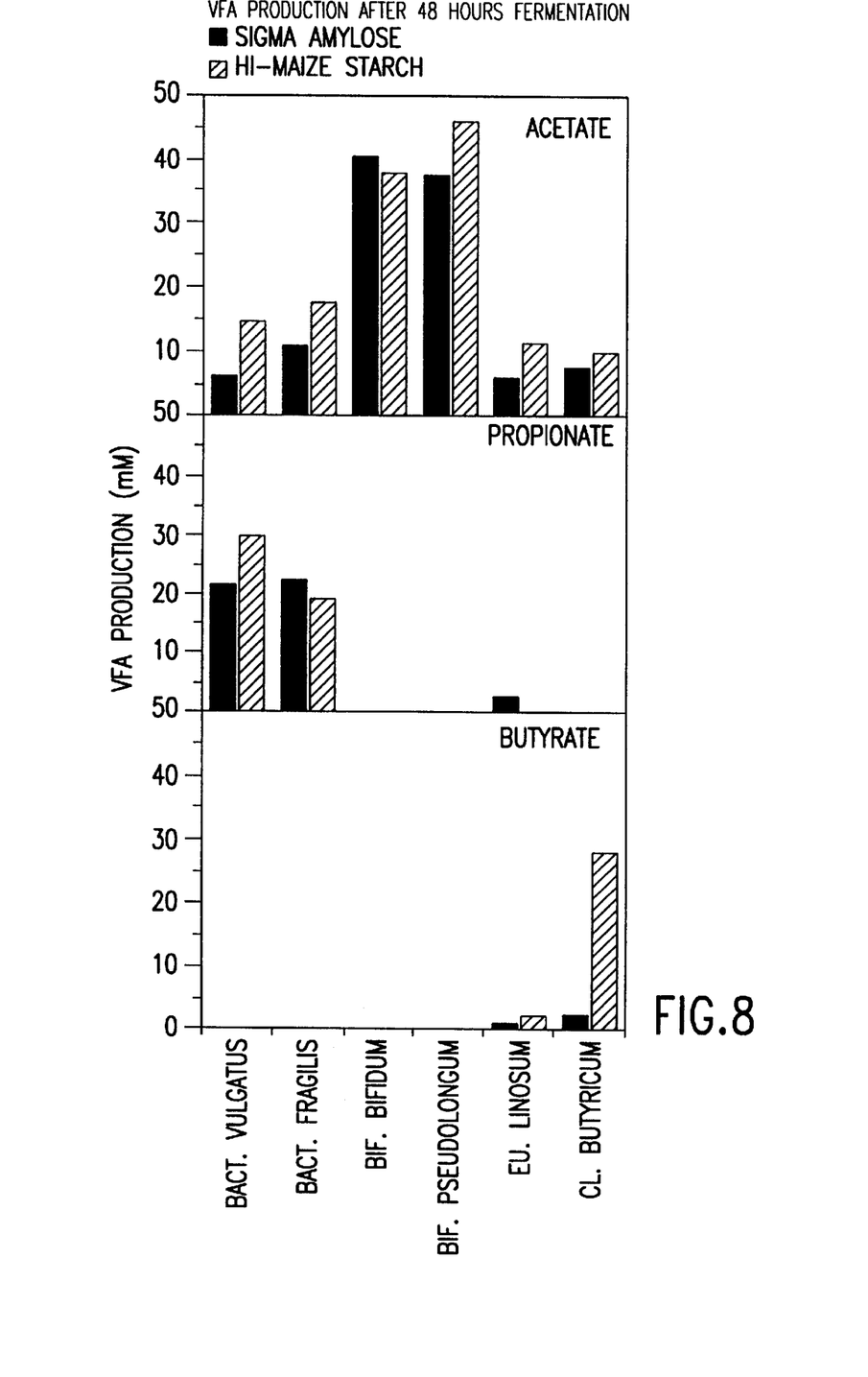
FIG. 8 is a graph of volatile fatty acid production for resistant starch (Hi-maize starch) and Sigma amylose when fermented with a number of bacteria.

In FIG. 8, there is shown the results obtained for volatile fatty acid production (VFA) for Hi-maize starch and Sigma amylose when fermented with a number of bacteria.

Figure 9A:
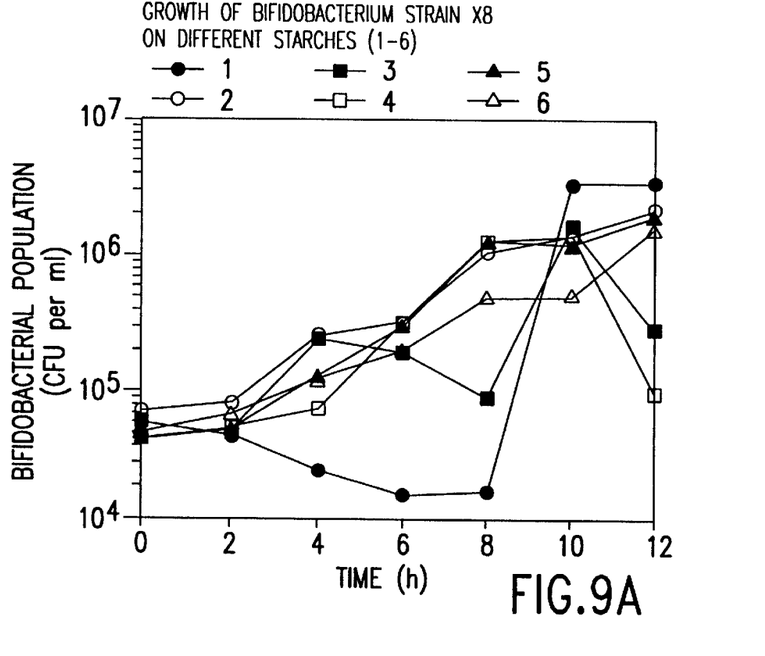
FIG. 9 is a graph of growth profile of bifidobacteria over time using a number of resistant starch substrates;.
Figure 9B:
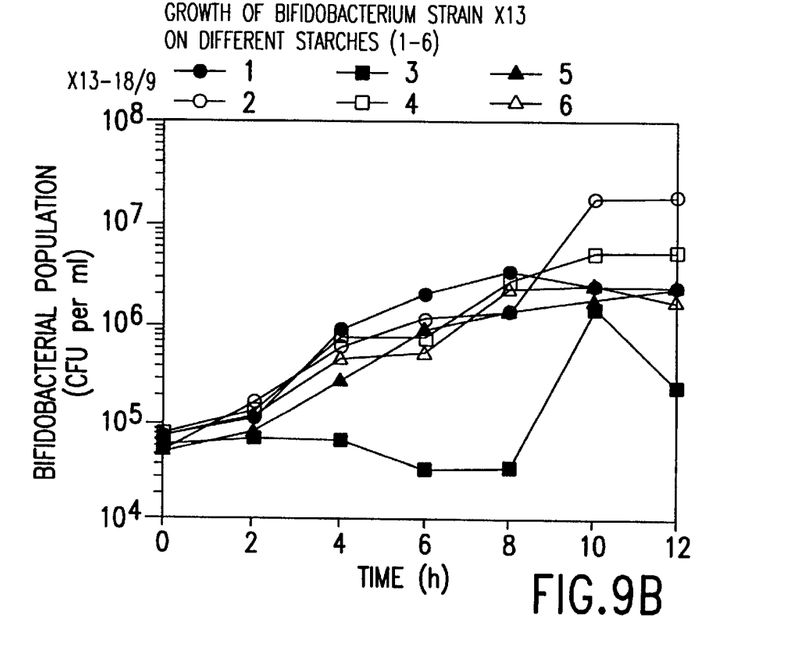

In FIG. 9, there is shown the growth profile of Bifidobacterium strains X8 and X13 over time using a number of resistant starch substrates.

Figure 10A:
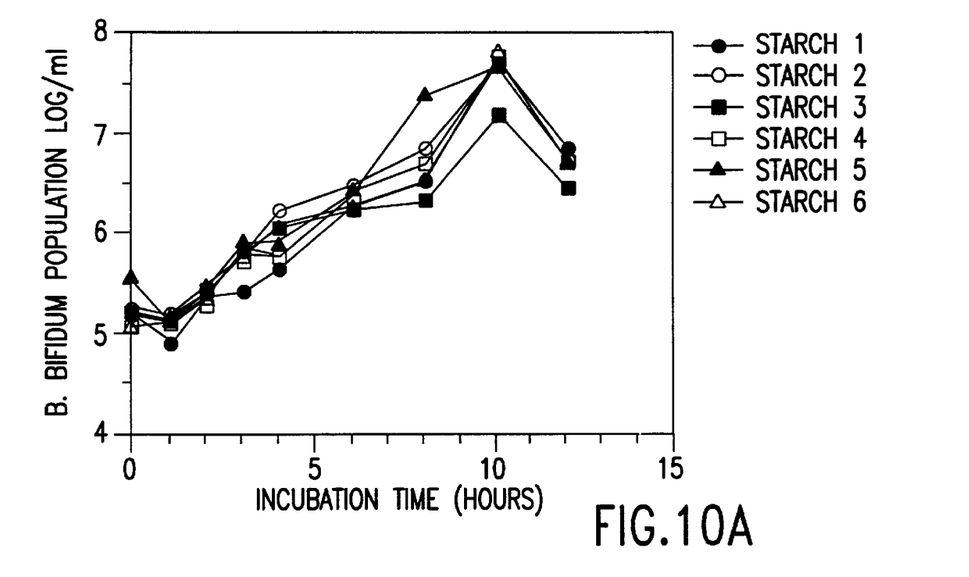
FIG. 10 is a graph of growth profile of B.bifidum and Cl.butyricum over time using a number of resistant starch substrates.
Figure 10B:
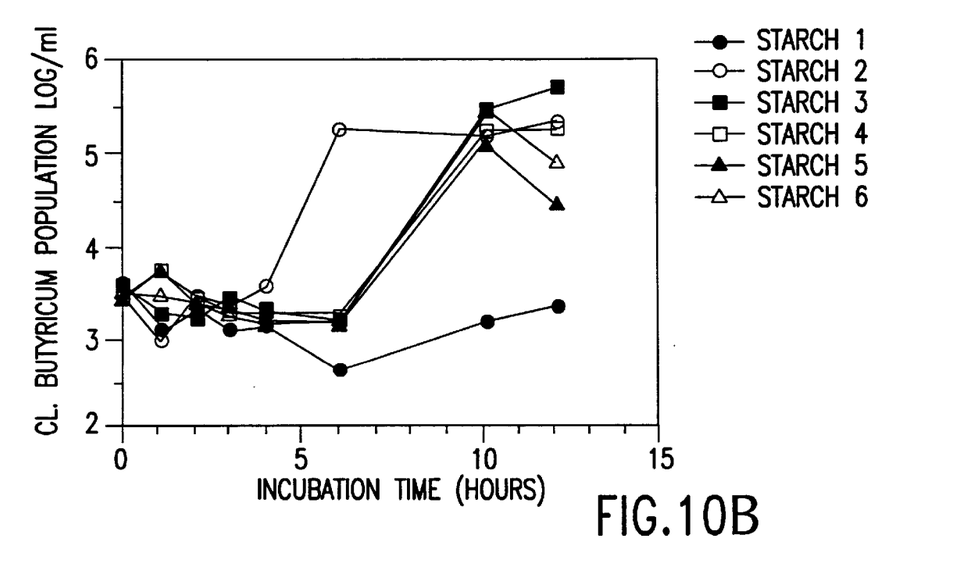

In FIG. 10, there is shown the growth profiles of B.bifidum and Cl.butyricum over time using the resistant starch substrates of FIG. 9.

TABLE 4

Fermentability of native and derivatised high amylose maize starch by different bacterial strains (residue of total carbohydrate present after 48 hours of anaerobic fermentation)

| | Total carbohydrate residue (mg/ml) | | | | | |
|---|---|---|---|---|---|---|
| Starch Type | 1 | 2 | 3 | 4 | 5 | 6 |
| Bifido strain X8AT1 | 6.43 | 4.99 | 5.57 | 4.68 | 4.97 | 6.41 |
| Cl. butyricum | 5.62 | 4.09 | 6.16 | 4.88 | 6.18 | 4.99 |

TABLE 4-continued

Fermentability of native and derivatised high amylose maize starch by different bacterial strains (residue of total carbohydrate present after 48 hours of anaerobic fermentation)

| | Total carbohydrate residue (mg/ml) | | | | | |
|---|---|---|---|---|---|---|
| Starch Type | 1 | 2 | 3 | 4 | 5 | 6 |
| B. bifidum | 6.70 | 5.20 | 6.09 | 5.79 | 6.00 | 6.68 |
| Medium control | 9.31 | 9.87 | 9.92 | 9.30 | 9.70 | 9.80 |

Starch type 1 = Hydroxypropylated
Starch type 2 = Acetylated
Starch type 3 = Octenyl succinated
Starch type 4 = Carboxymethylated
Starch type 5 = Succinated
Starch type 6 = Unmodified Observations Some strains, particularly those from the genus Bifidobacterium, Bacteroides, Eubacterium and Clostridium, demonstrated an ability to degrade the granular starch.

The products of these in vitro fermentations included short chain fatty acids (VFA) such as acetate, propionate and butyrate which are important in the maintenance and protection of the bowel and the body.

It is to be noted from FIG. 9 that each bacterial strain displayed individual growth profiles that demonstrated that the starch or chemically derivatised starch could act as the substrate for the fermentation.

In some cases such as that shown by Bifidobacterium strain X8 the ability to utilise the hydroxypropylated high amylose maize starch was not reflected in an increase in the population of Bifidobacterium strain X8 population until about 8 hours from the commencement of the incubation when the Bifidobacterium strain X8 population increased from about 4.2 log/ml to 6.2 log/ml after 10 hours.

Accordingly, the type or extent of the modification of the resistant starch may be used as a means by which to control either the rate or site of fermentation of the resistant starch in the gastrointestinal tract.

This is further demonstrated when the growth performance graphs shown in FIG. 10 are considered.

This allows for the possibility of selecting a modified resistant starch type to selectively target the promotion of bacterial growth in a region of the gastrointestinal tract.

Experiment 2

In this experiment, the ability of, for example Bifidobacterium, to adhere to the starch granules of native and derivatised high amylose maize starch granules for the purposes of transportation or fermentation was examined. The results shown in Table 5 indicate some differences based on the modified starch type.

TABLE 5

Percentage of starch granules with bacteria attached in aqueous suspension after simulated food processing (heated to 90° C. for 30 minutes)

| Starch Type | Starch granules with bacteria attached (%) | | | | | |
|---|---|---|---|---|---|---|
| | 1 | 2 | 3 | 4 | 5 | 6 |
| Bif. bifidium | 10 | 17.5 | 2.5 | 10 | 0 | 0 |
| Bif. strain X8AT2 | 25 | 40 | 10 | 32.5 | 47.5 | 10 |
| Bif. strain X13AT2 | 50 | 30 | 2.5 | 17.5 | 15 | 7.5 |

Starch type 1 = Hydroxypropylated
Starch type 2 = Acetylated
Starch type 3 = Octenyl succinated
Starch type 4 = Carboxymethylated
Starch type 5 = Succinated
Starch type 6 = Unmodified Experiment 3

In order to demonstrate that resistant starch can pass through to the large bowel and promote the growth of probiotics microorganisms, two feeding trials were conducted.

The first trial involved feeding mice known not to have any native caecal bifidobacteria, with a diet including Bifidobacterium strains as shown in Table 6.

TABLE 6

Diets for Mice Probiotic Feeding Experiments

| Test Groups | A | B | C | D | E |
|---|---|---|---|---|---|
| Starch | Waxy | HA | Carboxy-methyl | HA | None |
| | 400 | 400 | 400 | 400 | |
| Casein | 200 | 200 | 200 | 200 | |
| Canola oil | 25 | 25 | 25 | 25 | |
| Sunflower oil | 25 | 25 | 25 | 25 | |
| Sucrose | 150 | 150 | 150 | 150 | |
| Wheat bran | 100 | 100 | 100 | 100 | |
| Gelatin | 20 | 20 | 20 | 20 | |
| Mineral mix | 67 | 67 | 67 | 67 | |
| Vitamin mix | 13 | 13 | 13 | 13 | |
| Methionine | 2 | 2 | 2 | 2 | |
| Bacterial strain | X8AT2 | X8AT2 | X8AT2 | Bif. bifidum | X8AT2 |

* all weights in grams
Waxy: waxy maize starch
HA: high amylose maize starch
Carboxymethyl: Carboxymethylated high amylose maize starch Bacterial cultures (200 microlitres) were orally ingested by the mice with the starch containing meals.

The consumption of resistant starch resulted in an increase in faecal output and faecal dry matter plus a significant increase in the amount of starch detected in the mice faeces, as is shown in Table 7.

TABLE 7

Starch concentration in mice faeces

| | Starch in Faecal pool (% dry weight) | | |
|---|---|---|---|
| | Day 3–4 | Day 5–6 | Day 7–8 |
| Group A | 1.80 | −0.56 | 2.87 |
| Group B | 29.23 | 24.51 | 32.87 |
| Group C | 19.59 | 16.37 | 14.23 |
| Group D | 18.09 | 27.09 | 28.16 |
| Group E | 0.94 | 0.30 | −1.63 |

A comparison of the average viable bacterial counts in the mice faeces during the dosing period of the experiment, as shown in Table 8, revealed a significant increase in the number of bifidobacteria being excreted by the mice consuming resistant starch in the form of unmodified high amylose maize starch and modified (carboxymethylated) maize starch.

It is of further note that less carboxymethylated maize starch was found to be present in the faeces as compared with high amylose maize starch. This further demonstrates in vivo the differential utilisation of modified versus unmodified resistant starch as was mentioned in relation to the Table 4 and the results shown in FIGS. 9 and 10.

TABLE 8

Average of viable bacterial counts in the continued dosing period

| | Total bacteria output/day/mouse bifidobacteria | | |
|---|---|---|---|
| | Mean +− Std | Mean Diff. | F-test |
| Group A | 7.152 +− 0.96 | | |
| Group B | 7.965 +− 0.56 | | |
| Groups A–B | | −0.813 | $p < 0.05$ |
| Group C | 8.007 +− 0.50 | | |
| Groups A–C | | −0.855 | $p < 0.05$ |
| Group D | 9.434 +− 0.72 | | |
| Groups A–D | | −2.282 | $p < 0.05$ |
| Group E | 7.159 +− 0.61 | | |
| Groups A–E | | −0.007 | none |

The second trial involved feeding pigs a diet as shown in Table 9.

The formulations of these diets was prepared by blending the ingredients in a Hobart mixer at low speed for about 60 seconds to minimise any damage to the bacteria.

This trial (crossover design) was conducted involving 12 male pigs where one of two experimental diets, containing the probiotic Bifidobacterium longum, was fed for a period of one week followed by a cleaning out period where an antibiotic (Olaquindox broad spectrum for both gram positive and gram negative) diet was consumed.

TABLE 9

Experimental diets for the pigs

| Ingredient | Amount (g) | |
|---|---|---|
| Casein | 160 | 160 |
| Waxy maize starch | 498 | — |
| High amylose maize starch | — | 498 |
| Sucrose | 100 | 100 |
| Safflower | 40 | 40 |
| Wheatbran | 200 | 200 |
| Bifidobacterium longum 1941 | 20 | 20 |
| Vitamins & Minerals | 2 | 2 |

Bifidobacterium longum 1941 was consumed as a freeze dried powder with a viability of between $5.48 \times 10^9$ cfu/mg and $1.02 \times 10^{10}$ cfu/mg.

The experiment showed an increase of 0.92 (log10) in the numbers of bifidobacteria present in the faeces of individual pigs, as shown in Table 10.

TABLE 10

Summary of average Bif. longum counts in pig faeces on both diets

| Pig Number | Control Starch + Bif. longum (cfu/day) | Resistant Starch + Bif. longum (cfu/day) |
|---|---|---|
| 4 | $1.14 \times 10^{10}$ | $2.57 \times 10^{10}$ |
| 5 | $4.70 \times 10^{9}$ | $4.24 \times 10^{10}$ |
| 6 | $9.77 \times 10^{10}$ | $1.35 \times 10^{11}$ |
| 7 | $4.67 \times 10^{9}$ | $6.43 \times 10^{10}$ |
| 8 | $1.02 \times 10^{10}$ | $2.37 \times 10^{11}$ |
| 9 | $6.68 \times 10^{9}$ | $2.43 \times 10^{10}$ |
| 11 | $5.76 \times 10^{9}$ | $1.19 \times 10^{11}$ |
| 12 | $2.39 \times 10^{10}$ | $2.60 \times 10^{10}$ |
| 13 | $4.59 \times 10^{8}$ | $4.69 \times 10^{10}$ |
| 14 | $3.28 \times 10^{10}$ | $3.78 \times 10^{10}$ |
| 15 | $3.62 \times 10^{10}$ | $6.69 \times 10^{10}$ |

The level of faecal short chain fatty acids (acetate, propionate and butyrate) increased when the resistant starch was included in the diet but did not further increase when the probiotic was added. However the starch analysis performed on the faeces found that a larger percentage of starch was present in the pigs fed resistant starch that in the control diet (containing readily digestible waxy maize starch), but more importantly a significant drop in the percentage of starch present was observed when the resistant starch was fed in conjunction with the Bif.longum indicating that the Bif.longum was probably using the resistant starch as a substrate.

At the end of the final rotation, the experimental diets were maintained. The probiotic supplementation ceased. When the faeces were monitored over a four day period the level of Bif.longum experienced a rapid decline for the first two days and then appeared to achieve an equilibrium. This suggests that the diet may be promoting the colonising of the bifidobacteria in the bowel. Other reported experiments which did not include resistant starch found that the levels of bifidobacteria dropped completely within two days even after maintaining the experimental diet.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A probiotic composition comprising one or more probiotic microorganisms and a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for microorganisms in the large bowel or other regions of the gastrointestinal tract.

2. A two part probiotic composition comprising a first part which includes one or more probiotic microorganism s and a second part which includes a carrier, the carrier comprising a modified or unmodified resistant starch or mixtures thereof, which carrier acts as a growth or maintenance medium for microorganisms in the large bowel or other regions of the gastrointestinal tract.

3. A composition as in claim 1 wherein the starch is type RS1, RS2, RS3 or RS4.

4. A composition as in claim 3 wherein the resistant starch is selected from the group consisting of high amylose maize, rice, barley, wheat and legumes, or is derived from a source selected from the group consisting of potatoes and bananas.

5. A composition as in claim 1 wherein the resistant starch is modified.

6. A composition as in claim 5 wherein the resistant starch is hydroxy propylated, acetylated, octenyl succinated, carboxymethylated or succinated.

7. A composition as in claim 1 wherein the probiotic microorganism is in freeze dried form, concentrate form or frozen concentrate form.

8. A composition as in claim 7 wherein the resistant starch is freeze dried with the probiotic microorganism.

9. A composition as in claim 8 wherein the resistant starch is a concentration of 2 to 20% w/w.

10. A composition as in claim 1 wherein the resistant starch has been eroded or pitted.

11. A composition as in claim 1 wherein the probiotic microorganism is selected from the group consisting of Saccharomyces, Bifidobacterium, Bacteroides, Eubacterium, Clostridium, Lactobacillus, Fusobacterium, Propionibacterium, Streptococcus, Enteroccus, Lactococcus and Staphylococcus, Peptostreptococcus.

12. A composition as in claim 1 wherein the one or more probiotic microorganim and a modified resistant starch are selected such that bacterial growth is promoted in a selected region of the gastrointestinal tract.

13. A food composition including an effective amount of a probiotic composition as defined in claim 1.

14. A method of forming a probiotic composition comprising drying, blending, co-extruding, spray cooling, entrapment, adhesion or micro-encapsulating one or more probiotic microorganisms with a modified or unmodified resistant starch or mixtures thereof.

15. A method as in claim 14 wherein drying is by freeze drying, spouted bed drying or spray drying.

16. A method as in claim 15 wherein drying is by freeze drying.

17. A composition as in claim 4 wherein the amylose content is at least 50% w/w, or for rice starch, the amylose content is at least 27% w/w.

18. A composition as in claim 4, wherein the amylose content is at least 80% w/w.

19. A composition as in claim 17 wherein the resistant starch is maize starch.

* * * * *